(12) United States Patent
Claiborne et al.

(10) Patent No.: US 6,291,457 B1
(45) Date of Patent: Sep. 18, 2001

(54) COMPOUNDS HAVING CYTOKINE INHIBITORY ACTIVITY

(75) Inventors: Christopher F. Claiborne, Lansdale; David A. Claremon, Maple Glen; Nigel J. Liverton, Harleysville; Kevin T. Nguyen, Philadelphia, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/596,563

(22) Filed: Jun. 19, 2000

Related U.S. Application Data

(60) Provisional application No. 60/142,002, filed on Jul. 7, 1999.

(51) Int. Cl.[7] .................. A61K 31/5377; A61P 19/08; C07D 413/14
(52) U.S. Cl. .................. 514/235.8; 544/124; 546/274.1
(58) Field of Search .................. 544/124; 546/274.1; 514/235.8

(56) References Cited

U.S. PATENT DOCUMENTS 5,717,100   2/1998   Selnick et al. .

FOREIGN PATENT DOCUMENTS

| WO 98/56788 | 12/1998 | (WO) . |
| WO 99/01449 | 1/1999 | (WO) . |
| WO 99/03837 | 1/1999 | (WO) . |
| WO 00/26209 | 5/2000 | (WO) . |

OTHER PUBLICATIONS

Boehm et al, *J. Med. Chem.,* vol. 39, pp 3929–3937 (1996).*
G. Poli et al., Proc. Natl. Acad. Sci. USA, 87:782–785 (1990).
C. A. Dinarello, Rev. Infectious Diseases, 6 51–95 (1984).

* cited by examiner

*Primary Examiner*—Robert W. Ramsuer
(74) *Attorney, Agent, or Firm*—Shu Muk Lee; David L. Rose

(57) ABSTRACT

There are disclosed compounds of formula (I)

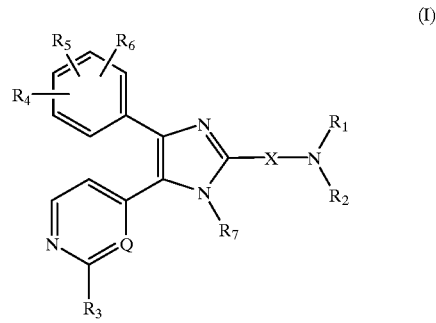

and pharmaceutically acceptable salts thereof which exhibit utility for the treatment of cytokine mediated diseases such as arthritis.

13 Claims, No Drawings

COMPOUNDS HAVING CYTOKINE INHIBITORY ACTIVITY

This application claims the benefit of Provisional application No. 60/142,002, filed Jul. 7, 1999.

BACKGROUND OF THE INVENTION

The present invention relates to substituted imidazole compounds which have cytokine inhibitory activity. Cytokine mediated diseases and cytokine inhibition, suppression and antagonism are used in the context of diseases or conditions in which excessive or unregulated production or activity of one or more cytokines occurs. Examples of cytokines which are effected typically include Interleukin-1 (IL-1), Interleukin-6 (IL6), Interleukin-8 (IL-8) and Tumor Necrosis Factor (TNF).

Interleukin-1 (IL-1) and Tumor Necrosis Factor (TNF) are produced by a variety of cells which are involved in immunoregulation and other physiological conditions.

There are many disease states in which IL-1 is implicated. Examples are rheumatoid arthritis, osteoarthritis, endotoxemia, toxic shock syndrome, acute and chronic inflammatory diseases, such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis and acute synovitis. Recent evidence also links IL-1 activity to diabetes.

Interleukin-1 has been demonstrated to mediate a variety of biological activities thought to be important in immunoregulation and other physiological conditions. [See, e.g., Dinarello et al., Rev. Infect. Disease, 6, 51 (1984)]. The known biological activities of IL-1 include the activation of T helper cells, induction of fever, stimulation of prostaglandin or collagenase production, neutrophil chemotaxis, induction of acute phase proteins and the suppression of plasma iron levels.

Excessive or unregulated tumor necrosis factor (TNF) production or activity has been implicated in mediating or exacerbating rheumatoid arthritis, rheumatoid spondylitis, osteoarthritis, gouty arthritis, and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcosis, bone resorption diseases, reperfusion injury, graft v. host rejection, allograft rejections, fever and myalgia due to infection, cachexia secondary to infection or malignancy, cachexia secondary to acquired immune deficiency syndrome (AIDS), AIDS related complex (ARC), keloid formation, scar tissue formation, Crohn's disease, ulcerative colitis and pyresis.

Monokines, such as TNF, have also been shown to activate HIV replication in monocytes and/or macrophages [See Poli, et al., Proc. Natl. Acad. Sci., 87:782–784 (1990)], therefore, inhibition of monokine production or activity aids in limiting HIV progression. TNF has been implicated in various roles with other viral infections, such as the cytomegalovirus (CMV), influenza virus and the herpes virus.

Interleukin-6 (IL-6) is a cytokine effecting the immune system and hematopoiesis. It is produced by several mammalian cell types in response to agents such as IL-1, and is correlated with disease states such as angiofollicular lymphoid hyperplasia.

Interleukin-8 (IL-8) is a chemotactic factor first identified and characterized in 1987. Many different names have been applied to IL-8, such as neutrophil attractant/activation protein-1 (NAP-1), monocyte derived neutrophil chemotactic factor (MDNCF), neutrophil activating factor (NAF), and T-cell lymphocyte chemotactic factor. Like IL-1, IL-8 is produced by several cell types, including mononuclear cells, fibroblasts, endothelial cells and ketainocytes. Its production is induced by IL-1, TNF and by lipopolysaccharide (LPS). IL-8 stimulates a number of cellular functions in vitro. It is a chemoattractant for neutrophils, T-lymphocytes and basophils. It induces histamine release from basophils. It causes lysozomal enzyme release and respiratory burst from neutrophils, and it has been shown to increase the surface expression of Mac-1 (CD11b/CD 18) on neutrophils without de novo protein synthesis.

There remains a need for compounds which are useful in treating cytokine mediated diseases, and as such, inhibit, suppress or antagonize the production or activity of cytokines such as IL-1, IL-6, IL-8 and TNF.

SUMMARY OF THE INVENTION

The present invention relates to compound I of the formula

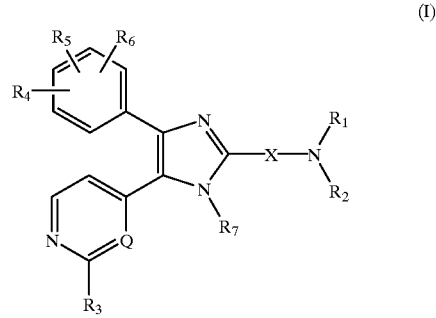

(I)

wherein

X is $C_1$–$C_6$ alkyl, said alkyl group optionally substituted by 1–3 groups selected from halogen, hydroxy, $CF_3$, $NH_2$ and $NO_2$; or a heterocyclic group connected to the imidazole ring by a direct bond or by $C_1$–$C_6$ alkyl;

$R_1$ and $R_2$ are independently hydrogen or $C_1$–$C_6$ alkyl, said alkyl group optionally substituted by 1–3 groups selected from halogen, hydroxy, $CF_3$, $NH_2$ and $NO_2$; or $R_1$ and $R_2$ taken together with the nitrogen atom represent an optionally substituted 4 to 10 membered non-aromatic heterocyclic ring containing at least one N atom, and optionally containing 1–2 additional N atoms and 0–1 O or S atom; or $R_2$ and X taken together represent an optionally substituted 4 to 10 membered non-aromatic heterocyclic ring containing at least one N atom, and optionally containing 1–2 additional N atoms and 0–1 O or S atoms;

Q is CH or N;

$R_3$ is hydrogen or NH($C_1$–$C_6$ alkyl)aryl;

$R_4$, $R_5$ and $R_6$ independently represent a member selected from the group consisting of hydrogen, halo, hydroxy, $CF_3$, $NH_2$, $NO_2$, $C_1$–$C_6$ alkyl, said alkyl group optionally substituted by 1–3 groups selected from halogen, hydroxy, $CF_3$, $NH_2$ and $NO_2$, $C_1$–$C_6$ alkoxy, said alkoxy group optionally substituted by 1–3 groups selected from halogen, hydroxy, $CF_3$, $NH_2$ and $NO_2$; $C_3$–$C_8$ cycloalkyl, said cycloalkyl group optionally substituted by 1–3 groups selected from halogen, hydroxy, $CF_3$, $NH_2$ and $NO_2$ or aryl, said aryl group optionally substituted by 1–3 groups selected from halogen, hydroxy, $CF_3$, $NH_2$ and $NO_2$;

$R_7$ is hydrogen or $C_1$–$C_6$ alkyl, said alkyl group optionally substituted by 1–3 groups selected from halogen, hydroxy, $CF_3$, $NH_2$ and $NO_2$;

or a pharmaceutically acceptable addition salt and/or hydrate thereof, or where applicable, a geometric or optical isomer or racemic mixture thereof.

This invention also relates to a pharmaceutical composition which is comprised of a compound of formula I as defined above in combination with a pharmaceutically acceptable carrier.

Also included in the invention is a method of treating a cytokine mediated disease in a mammal, comprising administering to a mammalian patient in need of such treatment an amount of a compound of formula I which is effective for treating said cytokine mediated disease.

DETAILED DESCRIPTION OF THE INVENTION

The present invention relates to compound I of the formula

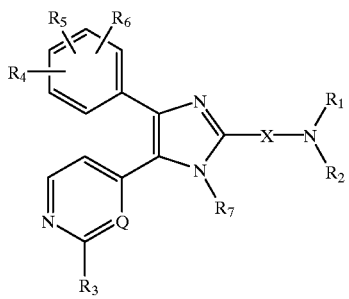

(I)

wherein
- X is $C_1$–$C_6$ alkyl, said alkyl group optionally substituted by 1–3 groups selected from halogen, hydroxy, $CF_3$, $NH_2$ and $NO_2$; or a heterocyclic group connected to the imidazole ring by a direct bond or by $C_1$–$C_6$ alkyl;
- $R_1$ and $R_2$ are independently hydrogen or $C_1$–$C_6$ alkyl, said alkyl group optionally substituted by 1–3 groups selected from halogen, hydroxy, $CF_3$, $NH_2$ and $NO_2$; or
- $R_1$ and $R_2$ taken together with the nitrogen atom represent an optionally substituted 4 to 10 membered non-aromatic heterocyclic ring containing at least one N atom, and optionally containing 1–2 additional N atoms and 0–1 O or S atom; or
- $R_2$ and X taken together represent an optionally substituted 4 to 10 membered non-aromatic heterocyclic ring containing at least one N atom, and optionally containing 1–2 additional N atoms and 0–1 O or S atoms;
- Q is CH or N;
- $R_3$ is hydrogen or $NH(C_1$–$C_6$ alkyl)aryl;
- $R_4$, $R_5$ and $R_6$ independently represent a member selected from the group consisting of hydrogen, halo, hydroxy, $CF_3$, $NH_2$, $NO_2$, $C_1$–$C_6$ alkyl, said alkyl group optionally substituted by 1–3 groups selected from halogen, hydroxy, $CF_3$, $NH_2$ and $NO_2$, $C_1$–$C_6$ alkoxy, said alkoxy group optionally substituted by 1–3 groups selected from halogen, hydroxy, $CF_3$, $NH_2$ and $NO_2$; $C_3$–$C_8$ cycloalkyl, said cycloalkyl group optionally substituted by 1–3 groups selected from halogen, hydroxy, $CF_3$, $NH_2$ and $NO_2$ or aryl, said aryl group optionally substituted by 1–3 groups selected from halogen, hydroxy, $CF_3$, $NH_2$ and $NO_2$;
- $R_7$ is hydrogen or $C_1$–$C_6$ alkyl, said alkyl group optionally substituted by 1–3 groups selected from halogen, hydroxy, $CF_3$, $NH_2$ and $NO_2$;

or a pharmaceutically acceptable addition salt and/or hydrate thereof, or where applicable, a geometric or optical isomer or racemic mixture thereof.

This invention also relates to a pharmaceutical composition which is comprised of a compound of formula I as defined above in combination with a pharmaceutically acceptable carrier.

Also included in the invention is a method of treating a cytokine mediated disease in a mammal, comprising administering to a mammalian patient in need of such treatment an amount of a compound of formula I which is effective for treating said cytokine mediated disease.

In a preferred embodiment, there is disclosed a compound of the formula

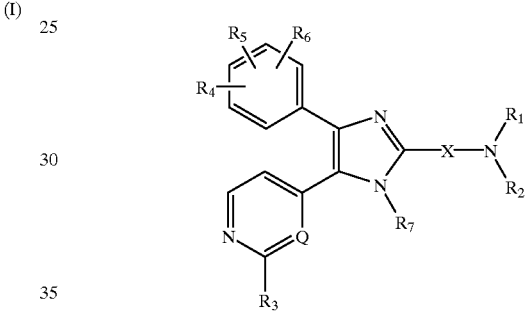

or a pharmaceutically acceptable salt thereof, wherein:
- Q is CH;
- X is $C_1$–$C_6$ alkyl; or
- $R_2$ and X taken together represent an azetidine group;
- $R_4$, $R_5$ and $R_6$ are independently hydrogen or $CF_3$;
- $R_7$ is $CH_3$;
- $R_1$ and $R_2$ are independently hydrogen or $C_1$–$C_6$ alkyl; or
- $R_1$ and $R_2$ taken together with the nitrogen atom form a morpholine group.

Representative species falling within the present invention include the following:

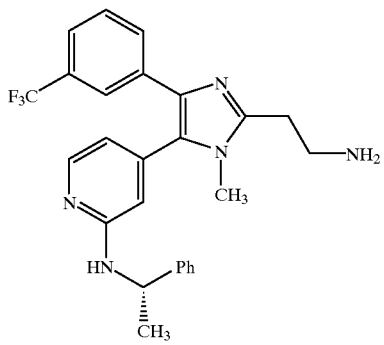

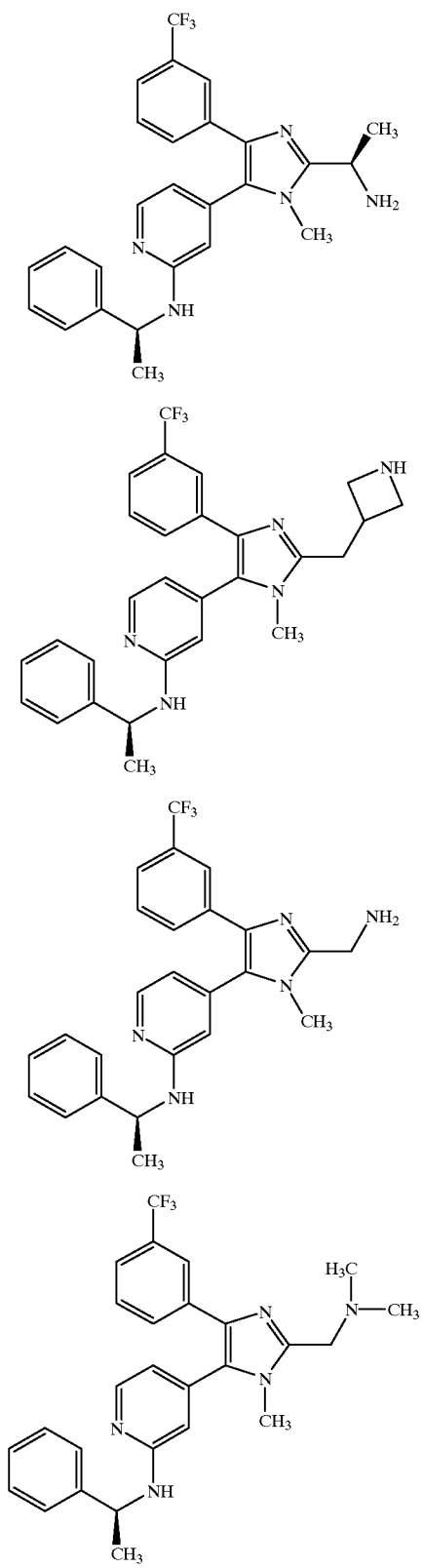
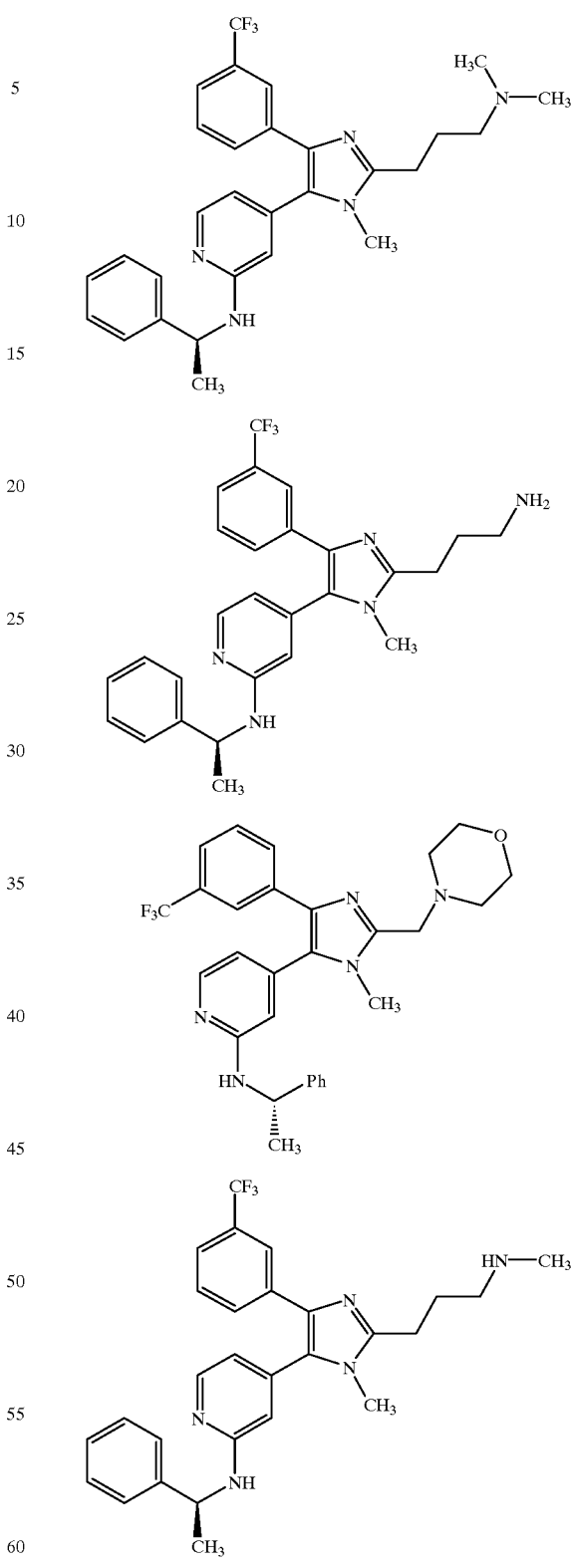

-continued

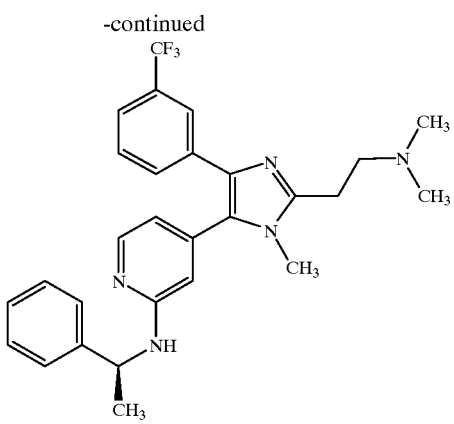

Unless otherwise stated or indicated, the following definitions shall apply throughout the specification and claims.

The term "alkyl" refers to a monovalent alkane (hydrocarbon) derived radical containing from 1 to 15 carbon atoms unless otherwise defined. It may be straight or branched, and when of sufficient size, e.g., C3–15 may be cyclic. Preferred straight or branched alkyl groups include methyl, ethyl, propyl, isopropyl, butyl and t-butyl. Preferred cycloalkyl groups include cyclopropyl, cyclopentyl and cyclohexyl.

Alkyl also includes an alkyl group substituted with a cycloalkyl group, such as cyclopropylmethyl. Alkyl also includes a straight or branched alkyl group The alkylene and monovalent alkyl portion(s) of the alkyl group can be attached at any available point of attachment to the cycloalkylene portion.

When substituted alkyl is present, this refers to a straight, branched or cyclic alkyl group as defined above, substituted with 1–3 groups as defined with respect to each variable.

The term "aryl" refers to aromatic rings e.g., phenyl, substituted phenyl and like groups as well as rings which are fused, e.g., naphthyl and the like. Aryl thus contains at least one ring having at least 6 atoms, with up to two such rings being present, containing up to 10 atoms therein, with alternating (resonating) double bonds between adjacent carbon atoms. The preferred aryl groups are phenyl and naphthyl. Aryl groups may likewise be substituted as defined below. Preferred substituted aryls include phenyl or naphthyl substituted with one or two groups.

The terms "heterocycloalkyl" and "heterocyclyl" refer to a cycloalkyl group (nonaromatic) in which one of the carbon atoms in the ring is replaced by a heteroatom selected from O, S(O)y or N, and in which up to three additional carbon atoms may be replaced by said heteroatoms. When three heteroatoms are present in the heterocycle, they are not all linked together.

Examples of heterocyclyls are piperidinyl, morpholinyl, azetidinyl, pyrrolidinyl, tetrahydrofuranyl, imidazolinyl, piperazinyl, pyrrolidin-2-one, piperidin-2-one and the like.

The term "halogen" or "halo" is intended to include fluorine, chlorine, bromine and iodine.

As used herein, the term "composition" is intended to encompass a product comprising the specified ingredients in the specified amounts, as well as any product which results, directly or indirectly, from combination of the specified ingredients in the specified amounts.

In addition, it is well known to those skilled in the art that many of the foregoing heterocyclic groups can exist in more than one tautomeric form. It is intended that all such tautomers be included within the ambit of this invention.

The optical isomeric forms, that is mixtures of enantiomers, e.g., racemates, or diastereomers as well as individual enantiomers or diastereomers of the instant compound are included. These individual enantiomers are commonly designated according to the optical rotation they effect by the symbols (+) and (−), (L) and (D), (l) and (d) or combinations thereof. These isomers may also be designated according to their absolute spatial configuration by (S) and (R), which stands for sinister and rectus, respectively.

The individual optical isomers may be prepared using conventional resolution procedures, e.g., treatment with an appropriate optically active acid, separating the diastereomers and then recovering the desired isomer. In addition, the individual optical isomers may be prepared by asymmetric synthesis.

Additionally, a given chemical formula or name shall encompass pharmaceutically acceptable addition salts thereof and solvates thereof, such as hydrates.

The compounds of the present invention, while effective themselves, may be formulated and administered in the form of their pharmaceutically acceptable addition salts for purposes of stability, convenience of crystallization, increased solubility and other desirable properties.

The compounds of the present invention may be administered in the form of pharmaceutically acceptable salts. The term "pharmaceutically acceptable salt" is intended to include all acceptable salts. Examples of acid salts are hydrochloric, nitric, sulfuric, phosphoric, formic, acetic, trifluoroacetic, propionic, maleic, succinic, malonic, methane sulfonic and the like which can be used as a dosage form for modifying the solubility or hydrolysis characteristics or can be used in sustained release or prodrug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, e.g. by reacting a free acid with a suitable organic or inorganic base, or alternatively by reacting a free base with a suitable organic or inorganic acid.

Also, in the case of an acid (—COOH) or alcohol group being present, pharmaceutically acceptable esters can be employed, e.g. methyl, ethyl, butyl, acetate, maleate, pivaloyloxymethyl, and the like, and those esters known in the art for modifying solubility or hydrolysis characteristics for use as sustained release or prodrug formulations.

The compounds of the present invention may have chiral centers other than those centers whose stereochemistry is depicted in formula I, and therefore may occur as racemates, racemic mixtures and as individual enantiomers or diastereomers, with all such isomeric forms being included in the present invention as well as mixtures thereof. Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The term "TNF mediated disease or disease state" refers to disease states in which TNF plays a role, either by production or increased activity levels of TNF itself, or by causing another cytokine to be released, such as but not limited to IL-1 or IL-6. A disease state in which IL-1, for instance is a major component, and whose production or action, is exacerbated or secreted in response to TNF, would therefore be considered a disease state mediated by TNF.

The term "cytokine" as used herein means any secreted polypeptide that affects the functions of cells and is a molecule which modulates interactions between cells in the immune, inflammatory or hematopoietic response. A cytokine includes, but is not limited to, monokines and lymphokines regardless of which cells produce them. Examples of cytokines include, but are not limited to, Interleukin-1 (IL-1), Interleukin-6 (IL-6), Interleukin-8 (IL-8), Tumor Necrosis Factor-alpha (TNF-α) and Tumor Necrosis Factor-beta (TNF-β).

By the term "cytokine interfering or cytokine suppresive amount" is meant an effective amount of a compound of formula I which will cause a decrease in the in vivo activity or level of the cytokine to normal or sub-normal levels, when given to the patient for the prophylaxis or therapeutic treatment of a disease state which is exacerbated by, or caused by, excessive or unregulated cytokine production or activity.

The compounds of the invention are prepared by the following general reaction scheme. All substituents are as defined above unless indicated otherwise. The preparation of specific compounds is illustrated in the examples section.

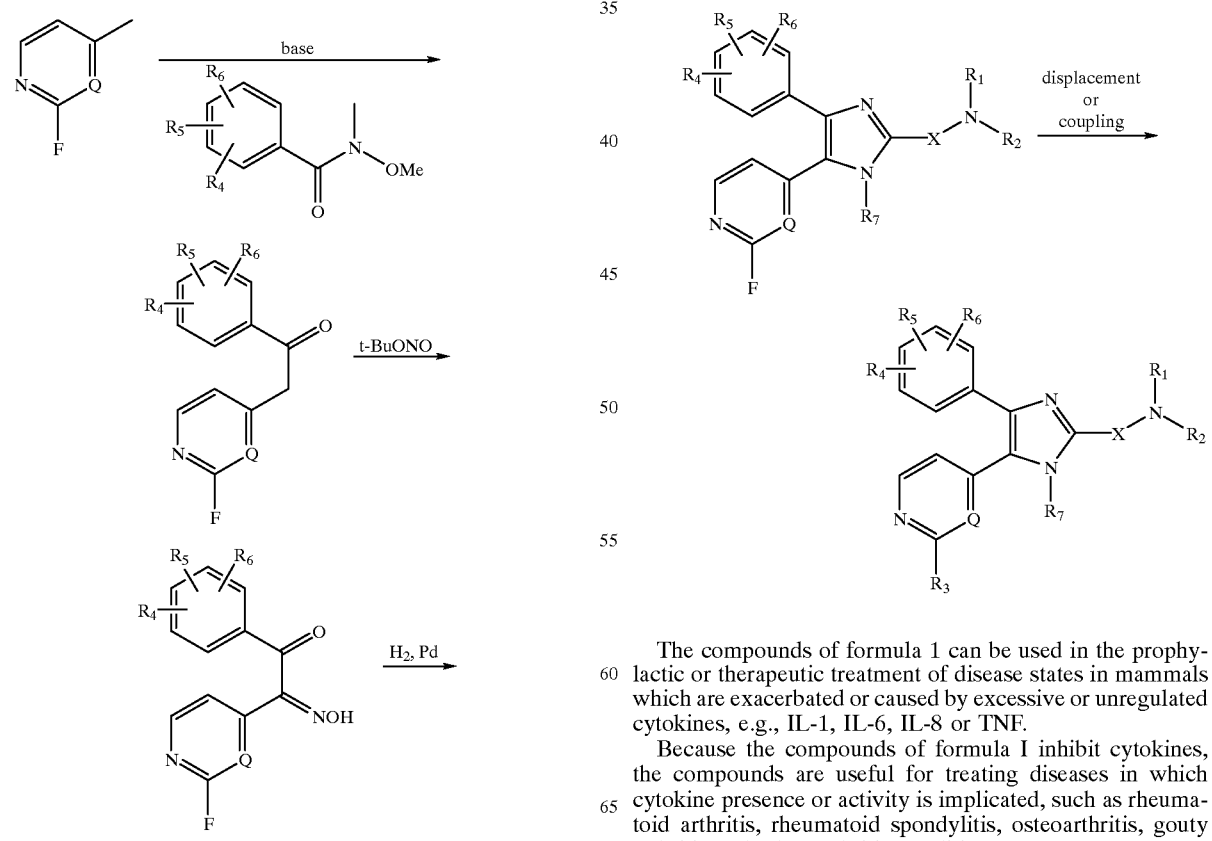

The compounds of formula 1 can be used in the prophylactic or therapeutic treatment of disease states in mammals which are exacerbated or caused by excessive or unregulated cytokines, e.g., IL-1, IL-6, IL-8 or TNF.

Because the compounds of formula I inhibit cytokines, the compounds are useful for treating diseases in which cytokine presence or activity is implicated, such as rheumatoid arthritis, rheumatoid spondylitis, osteoarthritis, gouty arthritis and other arthritic conditions.

The compounds of formula I are useful to treat disease states mediated by excessive or unregulated TNF production or activity. Such diseases include, but are not limited to sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, such as osteoporosis, reperfusion injury, graft v. host rejection, allograft rejection, fever, myalgia due to infection, cachexia secondary to infection or malignancy, cachexia secondary to acquired immune deficiency syndrome (AIDS), AIDS, ARC (AIDS related complex), keloid formation, scar tissue formation, Crohn's disease, ulcerative colitis, pyresis, AIDS and other viral infections, such as cytomegalovirus (CMV), influenza virus, and the herpes family of viruses such as Herpes Zoster or Simplex I and II.

The compounds of formula I are also useful topically in the treatment of inflammation such as in the treatment of rheumatoid arthritis, rheumatoid spondylitis, osteoarthritis, gouty arthritis and other arthritic conditions; inflamed joints, eczema, psoriasis or other inflammatory skin conditions such as sunburn; inflammatory eye conditions including conjunctivitis; pyresis, pain and other conditions associated with inflammation.

The compounds of formula I are also useful in treating diseases characterized by excessive IL-8 activity. These disease states include psoriasis, inflammatory bowel disease, asthma, cardiac and renal reperfusion injury, adult respiratory distress syndrome, thrombosis and glomerulonephritis.

The invention thus includes a method of treating psoriasis, inflammatory bowel disease, asthma, cardiac and renal reperfusion injury, adult respiratory distress syndrome, thrombosis and glomerulonephritis, in a mammal in need of such treatment, which comprises administering to said mammal a compound of formula I in an amount which is effective for treating said disease or condition.

When administered to a patient for the treatment of a disease in which a cytokine or cytokines are implicated, the dosage used can be varied within wide limits, depending upon the type of disease, the age and general condition of the patient, the particular compound administered, the presence or level of toxicity or adverse effects experienced with the drug and other factors. A representative example of a suitable dosage range is from as low as about 0.01 mg/kg to as high as about 100 mg/kg. However, the dosage administered is generally left to the discretion of the physician.

The methods of treatment can be carried out by delivering the compound of formula I parenterally. The term 'parenteral' as used herein includes intravenous, intramuscular, or intraperitoneal administration. The subcutaneous and intramuscular forms of parenteral administration are generally preferred. The instant invention can also be carried out by delivering the compound of formula I subcutaneously, intranasally, intrarectally, transdermally or intravaginally.

The compounds of formula I may also be administered by inhalation. By 'inhalation' is meant intranasal and oral inhalation administration. Appropriate dosage forms for such administration, such as an aerosol formulation or a metered dose inhaler, may be prepared by convention techniques.

The invention also relates to a pharmaceutical composition comprising a compound of formula I and a pharmaceutically acceptable carrier. The compounds of formula I may also be included in pharmaceutical compositions in combination with a second therapeutically active compound.

The pharmaceutical carrier employed may be, for example, either a solid, liquid or gas. Exemples of solid carriers include lactose, terra alba, sucrose, talc, gelatin, agar, pectin, acacia, magnesium stearate, stearic acid and the like. Examples of liquid carriers are syrup, peanut oil, olive oil, water and the like. Examples of gaseous carriers include carbon dioxide and nitrogen.

Similarly, the carrier or diluent may include time delay material well known in the art, such as glyceryl monostearate or glyceryl distearate, alone or with a wax.

A wide variety of pharmaceutical dosage forms can be employed. If a solid dosage is used for oral administration, the preparation can be in the form of a tablet, hard gelatin capsule, troche or lozenge. The amount of solid carrier will vary widely, but generally will be from about 0.025 mg to about 1 g. When a liquid dosage form is desired for oral administration, the preparation is typically in the form of a syrup, emulsion, soft gelatin capsule, suspension or solution. When a parenteral dosage form is to be employed, the drug may be in solid or liquid form, and may be formulated for administration directly or may be suitable for reconstitution.

Topical dosage forms are also included. Examples of topical dosage forms are solids, liquids and semi-solids. Solids would include dusting powders, poultices and the like. Liquids include solutions, suspensions and emulsions. Semi-solids include creams, ointments, gels and the like.

The amount of a compound of formula I used topically will, of course, vary with the compound chosen, the nature and severity of the condition, and can be varied in accordance with the discretion of the physician. A representative, topical, dose of a compound of formula I is from as low as about 0.01 mg to as high as about 2.0 g, administered one to four, preferably one to two times daily.

The active ingredient may comprise, for topical administration, from about 0.001% to about 10% w/w.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container aseptically. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous liquid, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surfactant such as sorbitan esters or polyoxyethylene derivatives thereof. Suspending agents such as natural gums, cellulose derivatives or inorganic materials such as silicas, and other ingredients such as lanolin may also be included.

The following examples illustrate the preparation of some of the compounds of the invention and are not to be construed as limiting the invention disclosed herein.

EXAMPLE 1

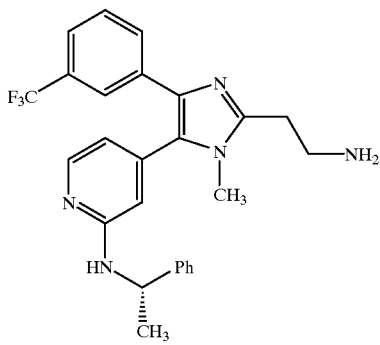

(S)-1-phenyl-N-{4-[2-(2-amino-ethyl)-3-methyl-5-(3-trifluoromethyl-phenyl)-3H-imidazol-4-yl]-pyridin-2-y}-ethylamine Step 1A 2-(2-Fluoropyridin-4-yl)-1-(3-trifluoromethylphenyl)-ethanone To a suspension of N,O-dimethylhydroxylamine hydrochloride (58.2 g, 0.60 mol) in dichloromethane (1 L) at 0° C., under argon, was added 3-trifluoromethylbenzoyl chloride (104.0 g, 0.50 mol), followed by a slow addition of triethylamine (152.3 mL, 1.09 mol). The reaction was aged for 30 min. at 5° C. and then allowed to warm to room temperature. TLC (1:1, ethyl acetate/hexane) showed the reaction to be complete. The reaction was washed with 5% aqueous citric acid (500 mL) and 5% aqueous sodium bicarbonate. The aqueous extracts were back extracted with methylene chloride (100 mL) and the combined methylene chloride extracts were dried over sodium sulfate, filtered and concentrated to an oil. The oil was redissolved in toluene (2×100 mL) and evaporated in vacuo to afford the Weinreb amide (114.7 g).

$^1$H NMR (300 MHz, CDCl3) d 7.98 (s, 1H, Ar), 7.89 (d, J=7.8 Hz, 1H, Ar), 7.72 (d, J=7.8 Hz, 1H, Ar), 7.55 (t, J=7.8 Hz, 1H, Ar), 3.55 (s, 3H, CH$_3$O), 3.39 (s, 3H, CH$_3$N).

To a stirring solution of diisopropylamine (17.69 mL, 0.135 mol) in anhydrous THF (200 mL) at −78° C., under argon, was added n-butyllithium (54.0 mL, 2.5M in hexane, 0.135 mol), followed after 5 min. by a solution of 2-fluoro-4-methylpyridine (10 g, 0.090 mol) in anhydrous THF (20 mL). After stirring for 15 min. at −78° C., a solution of N-methoxy-N-methyl-3-trifluoromethylbenzamide (23.08 g, 0.099 mol) in anhydrous THF (10 mL) was added to the reaction mixture which was then stirred for 5 min., and allowed to warm to 0° C. The reaction was quenched with water (400 mL), and extracted with ethyl acetate (3×200 mL). The ethyl acetate extracts were combined, dried over anhydrous sodium sulfate, filtered, and concentrated to an oil which was chromatographed on silica gel (1 kg), eluting with 20% ethyl acetate in hexane to give 21.6 g of the title compound.

$^1$H NMR (300 MHz, CDCl$_3$) d 8.25 (s, 1H, Pyr), 8.20 (d, J=5.1 Hz, 1H, Pyr), 8.18 (d, J=9.3 Hz, 1H, Pyr), 7.88 (d, J=7.8 Hz, Ar), 7.67 (t, J=7.8 Hz, 1H, Ar), 7.09 (d, J=5.1 Hz, 1H, Ar), 6.86 (s, 1H, Ar), 4.37 (s, 2H, PyrCH$_2$C).

Step 1B 1-(2-Fluoropyridin-4-yl)-2-(3-trifluoromethylphenyl)-ethane-1,2-dione 1-oxime To a mixture of 2-(2-fluoropyridin-4-yl)-1-(3-trifluoromethylphenyl)ethanone (10.80 g, 0.038 mol) in ethanol (200 mL), at −10° C., under argon, was added tert-butyl nitrite (5.0 mL, 0.042 mol) and hydrogen chloride (12.2 mL, 2.5M in ethanol, 0.031 mol) dropwise while maintaining the temperature below −5° C. Upon completion of addition, the reaction was allowed to warm to RT for 2 hrs. The reaction mixture was then concentrated in vacuo, diluted with water (100 mL), basified with saturated sodium bicarbonate (200 ml), and extracted with ethyl acetate (3×400 mL). The combined organic layers were washed with water (300 mL), dried with brine (300 mL) and anhydrous sodium sulfate, filtered and concentrated to yield 11.4 g of the title compound, as an oil.

$^1$H NMR (300 MHz, CDCl$_3$)d 8.31 (s, 1H, Ar), 8.29 (d, J=5.3 Hz, 1H, Pyr), 8.24 (d, J=7.8 Hz, 1H, Ar), 7.92 (d, J=8.1 Hz, 1H, Ar), 7.71 (t, J=7.8 Hz, 1H, Ar), 7.40 (d, J=5.1 Hz, 1H, Pyr), 7.23 (s, 1H, Pyr).

Step 1C 2-amino-2-(2-fluoropyridine-4-yl)-1-(3-trifluoromethylphenyl)ethanol

10% Palladium on carbon (3.0 g) was added to a solution of 1-(2-fluoropyridin4yl)-2-(3-trifluoromethylphenyl)-ethane-1,2-dione 1-oxime (8.0 g, 27 mmol) in ethanol (400 mL) at ambient temperature. The reaction vessel was vacuum purged, refilled with hydrogen and vigorously stirred for 10 hrs. After the reaction was complete, the solution was filtered through a pad of celite, and concentrated to give a solid. The residue was purified by recrystallization from methylene chloride and hexane to give 7.4 g of the title compound. m.p. 128–129° C.

$^1$H NMR (300 MHz, CD$_3$OD) d 8.01 (d, J=5.0 Hz, 1H, Ar), 7.53 (m, 1H, Ar), 7.49 (m, 2H, Ar), 7.43 (s, 1H, Ar), 7.06 (d, J=5.0 Hz, 1H, Ar), 6.86 (s, 1H, Ar), 4.96 (d, J=5.0 Hz, 1H, CH), 4.12 (d, J=5.0 Hz, 1H, CH).

Step 1D 2-(2-fluoropyridin-4-yl)-2-methylamino-1-(3-trifluoromethyl-phenyl)-ethanol 2-Amino-2-(2-fluoropyridin-4-yl)-1-(3-trifluoromethyl-phenyl)-ethanol (6 g, 20 mmol) was dissolved in ethyl formate (80 mL) and heated to reflux for 10 hrs under an argon atmosphere. The reaction mixture was cooled to ambient temperature and concentrated to yield the formamide as an oil. IH NMR (300 MH, CD$_3$OD) d 8.06 (m, 2 H, Ar), 7.55 (m, 3 H, Ar), 7.05 (m, 1 H, $^1$H NMR (300 MHz, CD$_3$OD) d 8.06 (m, 2H, Ar), 7.55 (m, 3H, Ar), 7.05 (m, 1H, Ar), 5.22 (d, J=5.7 Hz, 1H, CH), 5.10 (d, J=5.7 Hz, 1H, CH).

The formamide was azeotroped with toluene (2×100 mL) to remove trace amounts of ethyl formate and water. Reduction to the desired compound was carried out by drop-wise addition of borane-tetrahydrofuran complex (60 mL of a 1.0 M solution in THF, 60 mmol) to a solution the formamide product (20 mmol) in THF (60 mL) at ambient temperature. After 1 hr, the reaction was quenched by slow addition of the organic mixture to a vigorously stirring solution of aqueous hydrochloric acid (2.0 M, 500 mL). Stirring was continued for 3 h to assure complete dissociation of boron complexes. A solution of aqueous sodium hydroxide (10 M) was then added until a pH of 11 was achieved. The resulting mixture was extracted with ethyl acetate (2×300 mL), dried (sodium sulfate), and concentrated. The resulting residue was purified by filtration through a pad of silica gel (using 5% methanol and 0.5% ammonium hydroxide mixture in methylene chloride) to yield 5.3 g of a solid: mp 99–102° C.

$^1$H NMR (300 MHz, CD$_3$OD) d 7.99 (d, J=5.1 Hz, 1H, Ar), 7.50 (m, 1H, Ar), 7.45 (m, 2H, Ar), 7.38 (s, 1H, Ar), 7.02 (m, 1H, Ar), 6.83 (s, 1H, Ar), 5.09 (d, J=4.8 Hz, 1H, CH), 3.85 (d, J=4.8 Hz, 1H, CH), 2.22 (s, 3H, CH$_3$).

Step 1E
3-(Benzyloxycarbonyl-amino)-N-[1-(2-fluoro-pyridin-4-yl)-2-hydroxy-2-(3-trifluoromethyl-phenyl)-ethyl]-N-methyl-propionamide 1-Ethyl-3-(3-dimethylaminopropyl)carbodiimide hydrochloride (0.61 g, 3.2 mmol) was added to a solution of 2-(2-fluoro-pyridin-4-yl)-2-methylamino-1-(3-trifluoromethyl-phenyl)-ethanol (0.50 g, 1.6 mmol), 3-(benzyloxycarbonnyl-amino)-propanoic acid (0.53 g, 2.4 mmol), triethylamine (0.89 mL, 6.4 mmol), and 1-hydroxy-7-azabenzotriazole (0.43 g, 3.9 mmol) in dimethylformamide (10 mL) at ambient temperature. After 2 hrs stirring at ambient temperature, ethyl acetate was added (200 mL) followed by aqueous citric acid (50 mL of a 10% solution). The organic layer was then washed with aqueous sodium bicarbonate (50 mL of a sat. solution) and water (3×30 mL), dried (sodium sulfate), filtered, and concentrated. The crude residue was passed through a pad of silica gel (50% ethyl acetate in hexane) to remove minor impurities and yield 1.4 g of an oil.

$^1$H MMR (300 MHz, CD$_3$OD) d 8.17 (d, J=6.1 Hz, 1H, Pyr), 8.01 (s, 1H, Ar), 7.67 (d, J =7.8 Hz, 1H, Ar), 7.61 (d, J=7.8 Hz, 1H, Ar), 7.48 (t, J=7.8 Hz, 1H, Ar), 7.42–7.32 (m, 5H, Ar), 7.19 (d, J=7.1 Hz, 1H, Pyr), 7.05 (s, 1H, Pyr), 5.61 (d, J=8.8 Hz, 1H, PhCHOH), 5.40 (d, J=8.8 Hz, 1H, PhCHN), 5.03 (s, 2H, PhCH$_2$O), 3.42–3.25 (m, 4H, HNCH$_2$CH$_2$), 2.36 (s, 3H, CH$_3$N).

Step 1F
N-benzyloxycarbonyl-2-[5-(2-fluoro-pyridin-4-yl)-1-methyl-4-(3-trifluoromethyl-phenyl)-1H-imidazol-2-yl]-ethylamine Oxalyl chloride (0.34 mL, 3.9 mmol) was added to a solution of dimethyl sulfoxide (0.41 mL, 5.8 mmol) in methylene chloride (10 mL) at −78° C. After 20 min. at −78° C., 3-(benzyloxycarbonyl-amino)-N-[1-(2-fluoro-pyridin4-yl)-2-hydroxy-2-(3-trifluoromethyl-phenyl)ethyl]-N-methyl-propionamide (1.0 g, 1.9 mmol) in methylene chloride (10 mL) was added and the reaction solution was stirred at −78° C. for 2 hrs. Triethylamine (1.3 mL, 9.6 mmol) was added and the cooling bath was removed. The solution was diluted with ethyl acetate (150 mL), washed with aqueous ammonium chloride (75 mL) and brine (75 mL), dried (sodium sulfate), and concentrated. Some non-polar impurities were removed by passing the residue through silica gel, eluting with 50% ethyl acetate in hexane. The ketone was then transferred to a flask containing anhydrous ammonium trifluoroacetate (4 g) using a minimum amount of ether-methylene chloride. The mixture was placed under vacuum to remove the solvent, and then placed in a preheated oil bath (150° C.). Once all solid had melted and efficient stirring was achieved (approx. 10 min.) the formation of the imidazole was found to be complete. The heating bath was removed and the solids were partitioned between ethyl acetate and water (150/50 mL). The organic layer was dried (sodium sulfate), filtered, and concentrated. The product was purified by filtration through silica gel (imidazole is the least polar component) using ethyl acetate to yield 735 mg of a foam.

$^1$H NMR (300 MHz, CD$_3$OD) d 8.29 (d, J=5.4 Hz, 1H, Pyr), 7.69 (s, 1H, Ar), 7.53 (d, J=7.8 Hz, 1H, Ar), 7.52 (d, J=7.8 Hz, 1H, Ar), 7.45 (t, J=7.8 Hz, 1H, Ar), 7.35–7.22 (m, 6H, Ar), 7.05 (s, 1H, Pyr), 5.03 (s, 2H, PhCH$_2$O), 3.55 (t, J=6.8 Hz, 2H, HNCH$_2$CH), 3.51 (s, 3H, CH$_3$N), 3.03 (t, J=6.7 Hz, 2H, CCH$_2$CH$_2$).

Step 1G
(S)-1-phenyl-N-{4-[2-(2-(benzyloxycarbonyl-amino)ethyl)-3-methyl-5-(3-trifluoromethyl-phenyl)-3H-imidazol-4-yl]-pyridin-2-yl}-ethylamine N-Benzyloxycarbonyl-2-[5-(2-fluoro-pyridin-4-yl)-1-methyl-4-(3-trifluoromethyl-phenyl)-1H-imidazol-2-yl]-ethylamine (0.35 g, 0.70 mmol) was dissolved in S-(−)-a-methylbenzylamine (0.85 g, 7.0 mmol) and the reaction mixture was heated to 150° C. for 15 hrs. The heating bath was removed and the contents of the flask were partitioned between ethyl acetate (100 mL) and pH 4.5 buffer (50 mL composed of 10% citric acid that was treated with 10 N sodium hydroxide to achieve a pH of 4.5). The organic layer was dried (sodium sulfate), filtered, and concentrated. The residue was purified by silica gel chromatography to yield 315 mg of the desired product as an oil.

$^1$H NMR (300 MHz, CD$_3$OD) d 7.99 (d, J=5.4 Hz, 1H, Pyr), 7.69 (s, 1H, Ar), 7.49 (d, J=8.8 Hz, 1H, Ar), 7.47 (d, J=9.3 Hz, 1H, Ar), 7.36 (t, J=7.7 Hz, 1H, Ar), 7.33–7.13 (m, 10H, Ar), 6.43 (d, J=5.4 Hz, 1H, Pyr), 6.33 (s, 1H, Pyr), 5.03 (s, 2 H, PhCH$_2$O), 4.81 (q, J=6.8 Hz, 1H, PhCHCH$_3$), 3.50 (t, J=6.8 Hz, 2H, HNCH$_2$CH$_2$), 3.32 (s, 3H, CH$_3$N), 2.98 (t, J=6.7 Hz, 2H, CCH$_2$CH$_2$), 1.48 (d, J=6.8 Hz, 3H, PhCHCH$_3$).

Step 1H
(S)-1-phenyl-N-{4-[2-(2-amino-ethyl)-3-methyl-5-(3-trifluoromethyl-phenyl)-3H-imidazol-4-yl]-pyridin-2-yl}-ethylamine A solution of (S)-1-phenyl-N-{4-[2-(2-(benzyloxycarbonyl-amino)-ethyl)-3-methyl-5-(3-trifluoromethyl-phenyl)-3H-imidazol-4-yl]-pyridin-2-yl}-ethylamine (0.20 g, 0.33 mmol) in absolute ethanol (10 mL) was flushed with argon before 10% palladium on activated carbon (0.07 g) was added. This reaction mixture, flushed with hydrogen gas, was vigorously stirred under one atmosphere of hydrogen for 5 hrs, then filtered and concentrated. The residue was purified by silica gel chromatography to yield 146 mg of the desired product as an oil.

$^1$NMR (300 MHz, CD$_3$OD) d 7.99 (d, J=5.4 Hz, 1H, Pyr), 7.70 (s, 1H, Ar), 7.51 (d, J=7.6 Hz, 1H, Ar), 7.46 (d, J=7.8 Hz, 1H, Ar), 7.37 (t, J=7.7 Hz, 1H, Ar), 7.32–7.14 (m, 5H, Ar), 6.47 (d, J=5.4 Hz, 1H, Pyr), 6.35 (s, 1H, Pyr), 4.81 (q, J=7.1 Hz, 1H, PhCHCH$_3$), 3.35 (s, 3H, CH$_3$N), 3.06 (t, J=6.7 Hz, 2H, CH$_2$CH$_2$NH$_2$), 2.93 (t, J=7.0 Hz, 2H, CCH$_2$CH$_2$), 1.48 (d, J=6.8 Hz, 3H, PhCHCH$_3$).

EXAMPLE 2

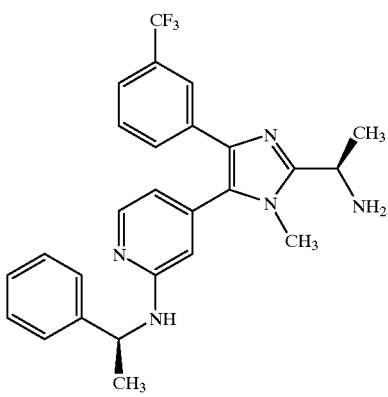

(S)-1-Phenyl-N-{4-[2-((R)-1-amino-ethyl)-3-methyl-5-(3-trifluoromethyl-phenyl)-3H-imidazol-4-yl]-pyridin-2-yl}-ethylamine The compound was prepared as described in example 1, replacing 3-(benzyloxycarbonnyl-amino)-propanoic acid with N-Cbz-D-Alanine in step 1E.

$^1$H NMR (300 MHz, CD$_3$OD) d 8.00 (d, J=5.4 Hz, 1H, Pyr), 7.72 (s, 1H, Ar), 7.51 (d, J=9.1 Hz, 1H, Ar), 7.48 (d, J=9.2 Hz, 1H, Ar), 7.37 (t, J=7.7 Hz, 1H, Ar), 7.31–7.22 (m, 4H, Ar), 7.16 (t, J=6.8 Hz, 1H, Ar), 6.46 (m, 1H, Pyr), 6.33 (s, 1H, Pyr), 4.80 (q, J=6.3 Hz, 1H, PhCHCH$_3$), 4.26 (q, J=6.6 Hz, 1H, NH$_2$CHCH$_3$), 3.41 (s, 3H, NCH$_3$), 1.53 (d, J=6.8 Hz, 3H, PhCHCH$_3$), 1.48 (d, J=6.8 Hz, 3H, NH$_2$CHCH$_3$); MS (FAB) Calcd for C$_{26}$H$_{26}$F$_3$N$_5$ (M+H$^+$) 466.2, found 466.3

EXAMPLE 3

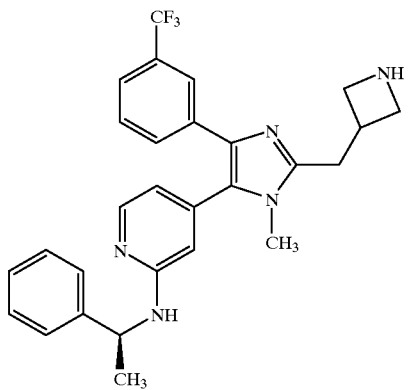

(S)-1-Phenyl-N-{4-[2-(azetidin-3-yl-methyl)-3-methyl-5-(3-trifluoromethyl-phenyl)-3H-imidazol-4-yl]-pyridin-2-yl}-ethylamine Compound was prepared as described in example 1, replacing 3-(benzyloxycarbonnyl-amino)-propanoic acid with 3-carboxymethyl-azetidine-1-carboxylic acid benzyl ester (synthesis described below) in step E.

$^1$H NMR (300 MHz, CD$_3$OD) d 7.99 (d, J=5.1 Hz, 1H, Pyr), 7.67 (s, 1H, Ar), 7.49 (d, J=8.3 Hz, 1H, Ar), 7.46 (d, J=9.5 Hz, 1H, Ar), 7.36 (t, J=7.7 Hz, 1H, Ar), 7.32–7.13 (m, 5H, Ar), 6.45 (d, J=5.1 Hz, 1H, Pyr), 6.33 (s, 1H, Pyr), 4.80 (q, J=6.8 Hz, 1H, PhCHCH$_3$), 3.94 (m, 2H, CHCH$_2$NH), 3.69 (m, 2H, CHCH$_2$NH), 3.34 (s, 3H, NCH$_3$), 3.10 (d, J=7.6 Hz, 2H, CCH$_2$CH), 3.04 (m, 1H, CH$_2$CHCH$_2$), 1.48 (d, J=6.8 Hz, 3H, PhCHCH$_3$); MS (FAB) Calcd for C$_{28}$H$_{28}$F$_3$N$_5$ (M+H$^+$) 492.2, found 492.3

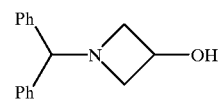

Step 3A
1-Benzhydryl-azetidin-3-ol Hydrochloride

A mixture of benzhydrylamine (56 g, 306 mmol), and epichlorohydrin (24 mL, 306 mmol) in methanol (150 mL) was stirred at 24° C. under argon for 3 days, then refluxed for 3 days. This reaction mixture was concentrated in vacuo, the residue stirred in acetone (500 mL) and filtered to give the crystaline salt as the title compound (78 g).

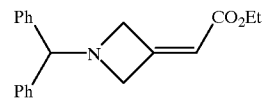

Step 3B
(1-Benzhydryl-azetidin-3-ylidene)-acetic Acid Ethyl Ester

To a stirring solution of DMSO (5.3 mL, 75 mmol) in methylene chloride (100 mL) at -78° C. under argon was added oxalyl chloride (4.6 mL, 53 mmol) dropwise. After stirring for 30 min., a solution of 1-benzhydryl-azetidin-3-ol hydrochloride (12) (10 g, 36 mmol) in methylene chloride (10 mL) was added dropwise. The reaction mixture was stirred for 1 hr at -78° C. before triethylamine (18 mL, 128 mmol) was added. The ice bath was removed and the reaction quenched with saturated ammonium chloride (75 mL) at 0° C., then extracted with ethyl acetate (3×150 mL). The combined ethyl acetate layer was washed with water (100 mL), brine (100 mL), dried over anhydrous sodium sulfate, filtered, and concentrated. The residue was stirred in ethyl acetate and hexane, filtered to give 1-benzhydrylazetidin-3-one (9 g, 33 mmol, 92%). To a stirring solution of the resulting 1-benzhydryl-azetidin-3-one (8.3 g, 30 mmol) in methylene chloride (120 mL) was added triethylamine (6.4 mL, 45 mmol), and carbethoxymethylene triphenylphosphorane (15.9 g, 45 mmol). This reaction mixture was stirred under argon at room temperature for 2 hrs., then quenched with acetone (1 mL), and concentrated in vacuo. The residue was stirred in 20% ethyl acetate in hexane (20 mL) as triphenyl phosphine oxide precipitated. The mixture was then filtered and concentrated. The crude product was chromatographed on silica gel, eluting with 50:40:10 methylene chloride:hexane:ether to give 9.3 g of the title compound.

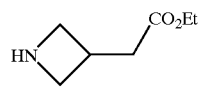

Step 3C
Azetidin-3-yl-acetic Acid Ethyl Ester

To a solution of (1-benzhydrylazetidin-3-ylidene)-acetic acid ethyl ester (5.0 g, 16 mmol) in ethanol (200 mL) was added palladium hydroxide on carbon (1.5 g). This mixture was vigorously shaken under a 50 psi hydrogen atmosphere for 24 hrs, then filtered and concentrated to give an oil, used without additional purification.

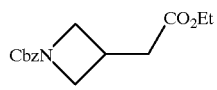

Step 3D
3-Ethoxycarbonylmethyl-azetidine-1-carboxylic Acid Benzyl Ester

To a stirring mixture of azetidin-3-yl-acetic acid ethyl ester (1.0 g, 6.98 mmol), in saturated aqueous sodium bicarbonate (5 mL) and THF (5 mL) at 0° C. was added carbobenzyloxy chloride (1.1 mL, 7.68 mmol) dropwise. The ice bath was removed and the reaction mixture was stirred at room temperature for 2 hrs, then extracted with ethyl acetate acetate (3×20 mL). The combined ethyl acetate layer was washed with water (10 mL), brine (10 mL), dried over anhydrous sodium sulfate, filtered, and concentrated. The residue was chromatographed on silica gel, eluting with 20% ethyl acetate in hexane to give 0.30 g of the title compound.

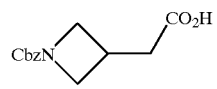

Step 3E
3-Carboxymethyl-azetidine-1-carboxylic Acid Benzyl Ester

A solution of 3-ethoxycarbonylmethylazetidine-1-carboxylic acid benzyl ester (0.30 g, 1.1 mmol), and lithium hydroxide monohydrate (0.091 g, 2.2 mmol) in TBF (3 mL) and water (1 mL) was stirred under argon at room temperature for 1 hr. After acidification with 2 M aqueous hydrochloric acid (10 mL), the reaction mixture was extracted with ethyl acetate (3×20 ml). The combined ethyl acetate layers were washed with water (10 mL), brine (10 mL), dried over anhydrous sodium sulfate, filtered, and concentrated to give 0.27 g of the title compound.

EXAMPLE 4

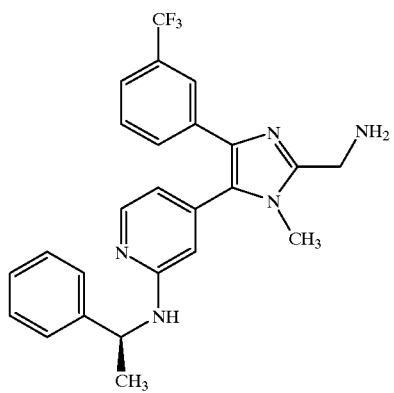

(S)-1-Phenyl-N-{4-[2-aminomethyl-3-methyl-5-(3-trifluoromethylphenyl)-3H-imidazol-4-yl]-pyridin-2-yl}-ethylamine The compound was prepared as described in example 1, replacing 3-(benzyloxycarbonylamino)propanoic acid with N-Cbz-glycine in step 1E.

$^1$H NMR (300 MHz, CD$_3$OD) d 8.01 (d, J=5.4 Hz, 1H, Pyr), 7.72 (s, 1H, Ar), 7.52 (d, J=7.6Hz, 1H,Ar),7.47 (d, J=7.8 Hz, 1H, Ar),7.37 (t, J=7.6 Hz, 1H, Ar), 7.32–7.22 (m, 4H, Ar), 7.16 (t, J=7.1 Hz, 1H, Ar), 6.46 (dxd, J=5.4 & 1.5 Hz, 1H, Pyr), 6.35 (s, 1H, Pyr), 4.82 (q, J=6.8 Hz, 1H, PhCHCH$_3$), 3.96 (s, 2H, CCH$_2$NH$_2$), 3.40 (s, 3H, CH$_3$N), 1.48 (d, J=6.8 Hz, 3H, PhCHCH$_3$); MS (FAB) Calcd for C$_{25}$H$_{24}$F$_3$N$_5$ (M+H$^+$) 451, found 452

EXAMPLE 5

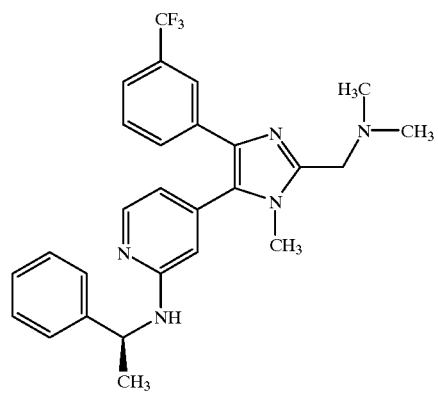

(S)-1-Phenyl-N-{4-[2-(dimethylamino)methyl-3-methyl-5-(3-trifluoromethyl-phenyl)-3H-imidazol-4-yl]-pyridin-2-yl}-ethylamine The compound was prepared as described in example 1, replacing 3-(benzyloxycarbonylamino)propanoic acid with 3-carboxymethyl-azetidine-1-carboxylic acid benzyl ester in step 1E.

$^1$H NMR (300 MHz, CD$_3$OD) d 8.00 (d, J=5.4 Hz, 1H, Pyr), 7.71 (s, 1H, Ar), 7.51 (d, J=7.8 Hz, 1H, Ar), 7.47 (d, J=7.8 Hz, 1H, Ar), 7.37 (t, J=7.8 Hz, 1H, Ar), 7.32–7.22 (m, 4H, Ar), 7.16 (t, J=7.1 Hz, 1H, Ar), 6.46 (dxd, J=5.4 & 1.5 Hz, 1H, Pyr), 6.37 (s, 1H, Pyr), 4.83 (q, J=7.1 Hz, 1H, PhCHCH$_3$), 3.61 (s, 2H, CCH$_2$N), 3.45 (s, 3H, CH$_3$N), 2.31 (s, 6H, N(CH$_3$)$_2$), 1.48 (d, J=6.8 Hz, 3H, PhCHCH$_3$); MS (FAB) Calcd for C$_{27}$H$_{28}$F$_3$N$_5$ (M+H$^+$) 479.2, found 480.3

EXAMPLE 6

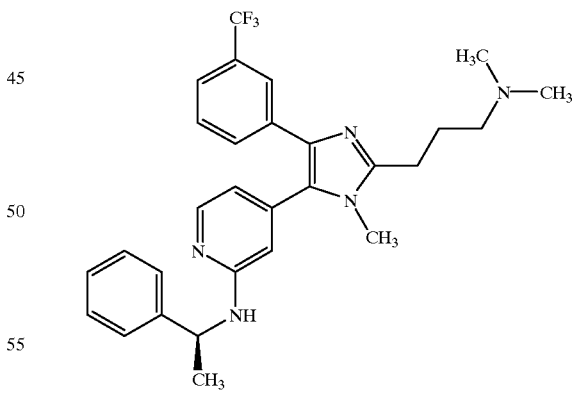

(S)-1-Phenyl-N-{4-[2-(3-dimethylamino-propyl)-3-methyl-5-(3-trifluoromethylphenyl)-3H-imidazol-4-yl]-pyridin-2-yl}-ethylamine The compound was prepared as described in example 1, replacing 3-(benzyloxycarbonylamino)propanoic acid with N-Cbz-GABA in step 1E. Then a mixture of (S)-1-phenyl-N-{4-[2-(3-amino-propyl)-3-methyl-5-(3-trifluoromethylphenyl)-3H-imidazol-4-yl]-pyridin-2-yl}-ethylamine (0.10 g, 0.21 mmol), formaldehyde (0.10 g, 1.25 mmol), and palladium on activated carbon (10%) (0.03 g) in methanol (5 mL) was vigorously stirred under 1 atm hydrogen for 6 hrs. The reaction mixture was then filtered, and concentrated. The residue was chromatographed on silica gel, eluting with 90:10:1 $CH_2Cl_2$:MeOH:$NH_4OH$ to give 0.087 g of the title compound.

$^1$H NMR (300 MHz, $CD_3OD$) d 8.00 (d, J=5.4 Hz, 1H, Pyr), 7.68 (s, 1H, Ar), 7.50 (d, J=7.5 Hz, 1H, Ar), 7.47 (d, J=8.6 Hz, 1H, Ar), 7.38 (t, J=7.7 Hz, 1H, Ar), 7.32–7.23 (m, 4H, Ar), 7.16 (t, J=6.9 Hz, 1H, Ar), 6.46 (dxd, J=5.4 & 1.5 Hz, 1H, Pyr), 6.34 (s, 1H, Pyr), 4.81 (q, J=6.8 Hz, 1H, PhCHCH$_3$), 3.34 (s, 3H, CH$_3$N), 2.83 (t, J=7.7 Hz, 2H, CH$_2$CH$_2$N), 2.55 (t, J=7.7 Hz, 2H, CCH$_2$CH$_2$), 2.35 (s, 6H N(CH$_3$)2), 1.97 (quin, J=7.5 Hz, 2H, CH$_2$CH$_2$CH$_2$), 1.48 (d, J=6.8 Hz, 3H, PhCHCH$_3$); MS (FAB) Calcd for $C_{29}H_{32}F_3N_5$ (M+H$^+$) 507.3, found 508.4

EXAMPLE 7

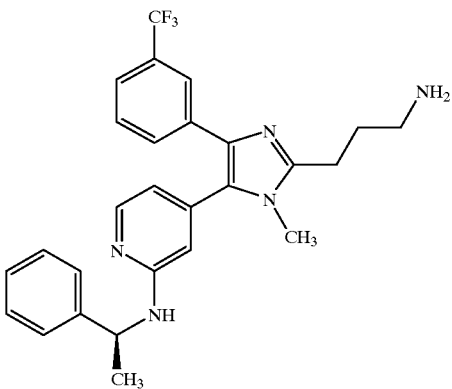

(S)-1-Phenyl-N-{4-[2-(3-amino-propyl)-3-methyl-5-(3-trifluoromethyl-phenyl)-3H-imidazol-4-yl]-pyridin-2-yl}-ethylamine The compound was prepared as described in example 1, replacing 3-(benzyloxycarbonylamino)propanoic acid with N-Cbz-GABA in step 1E.

1H NMR (300 MHz, $CD_3OD$) d 8.00 (d, J=5.1 Hz, 1H, Pyr), 7.69 (s, 1H, Ar), 7.49 (d, J=7.6 Hz, 1H, Ar), 7.47 (d, J=5.9 Hz, 1H, Ar), 7.37 (t, J=7.8 Hz, 1H, Ar), 7.32–7.22(m, 4H, Ar),7.16 (t,J=6.9 Hz, 1H, Ar), 6.46 (dxd, J=5.4 & 1.5 Hz, 1H, Pyr), 6.34 (s, 1H, Pyr), 4.81 (q, J=6.8 Hz, 1H, PhCHCH$_3$), 3.35 (s, 3H, CH$_3$N), 2.94 (t, J=7.2 Hz, 2H, CH$_2$CH$_2$NH$_2$), 2.89 (t, J=7.3 Hz, 2H, CCH$_2$CH$_2$), 2.04 (quin, J=7.3 Hz, 2H, CH$_2$CH$_2$CH$_2$), 1.49 (d, J=6.8 Hz, 3H, PhCHCH$_3$); MS (FAB) Calcd for $C_{27}H_{28}F_3N_5$ (M+H$^+$) 479.2, found 480.3

EXAMPLE 8

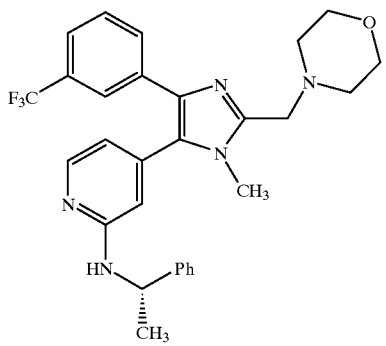

{4-[3-methyl-2-(morpholin-4-ylmethyl)-5-(3-trifluoromethylphenyl)-3H-imidazol-4-yl]-pyridin-2-yl}-(1-phenylethyl)-amine The title compound was prepared as described in example 1, replacing 3-(benzyloxycarbonylamino)propanoic acid with morpholin-4-yl-acetic acid (from comercially available methyl morpholinoacetate by aqueous acid hydrolysis (6N HCl reflux 2 h)) in step 1E and omission of deprotection step 1H.

$^1$H NMR (300 MHz, $CD_3OD$) d 8.12 (d, J=5.4 Hz, 1H, Pyr), 7.79 (s, 1H, Ar), 7.47 (d, J=8.0 Hz, 1H, Ar), 7.39 (d, J=8.0 Hz, 1H, Ar), 7.25 (m, 6H, Ar), 6.47 (d, J=5.4 Hz, 1H, Pyr), 6.07 (s, 1H, Pyr), 5.44 (d, J=5.6, 1H, NH), 4.62 (m, 1H, PhCHCH$_3$), 3.70 (m, 4H, CH$_2$), 3.64 (s, 2H, CH$_2$), 3.26 (s, 3H, CH$_3$), 2.51 (m, 4H, CH$_2$), 1.54 (d, J=6.0 Hz, 3H, PhCHCH$_3$). MS (FAB) Calcd for $C_{29}H_{30}F_3N_5O$ (M+H$^+$) 522.2, found 522.2

EXAMPLE 9

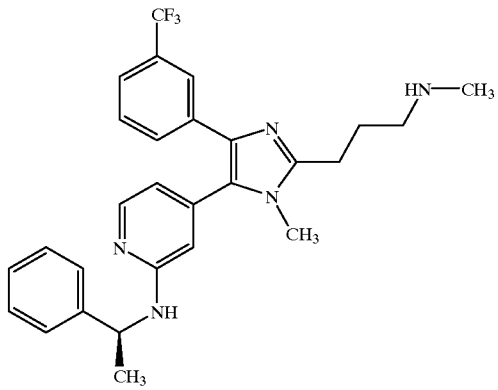

(S)-1-Phenyl-N-{4-[2-(3-methylaminopropyl)-3-methyl-5-(3-trifluoromethylphenyl)-3H-midazol-4-yl]-pyridin-2-yl}-ethylamine The compound was prepared as described in example 7 and then methylated as shown in step 1D.

$^1$H NMR (300 MHz, $CD_3OD$) d 8.00 (d, J=5.4 Hz, 1H, Pyr), 7.69 (s, 1H, Ar), 7.49 (d, J=7.3 Hz, 1H, Ar), 7.47 (d,J=6.4 Hz, 1H, Ar), 7.37 (t, J=7.7 Hz, 1H, Ar), 7.32–7.23 (m, 4H, Ar), 7.16 (t, J=6.9 Hz, 1H, Ar), 6.46 (dxd, J=5.4 & 1.5 Hz, 1H, Pyr), 6.34 (s, 1H, Pyr), 4.81 (q, J=6.4 Hz, 1H, PhCHCH$_3$), 3.36 (s, 3H, CH$_3$N), 2.87 (t, J=7.5 Hz, 2H, CH2CH$_2$NH), 2.81 (t, J=7.3 Hz, 2H, CCH$_2$CH$_2$), 2.49 (s, 3H, NHCH$_3$), 2.00 (quin, J=7.3 Hz, 2H, CH$_2$CH$_2$CH$_2$), 1.48 (d, J=6.8 Hz, 3H, PhCHCH$_3$); MS (FAB) Calcd for C$_{28}$H$_{30}$F$_3$N$_5$ (M+H$^+$) 493.2, found 494.3

EXAMPLE 10

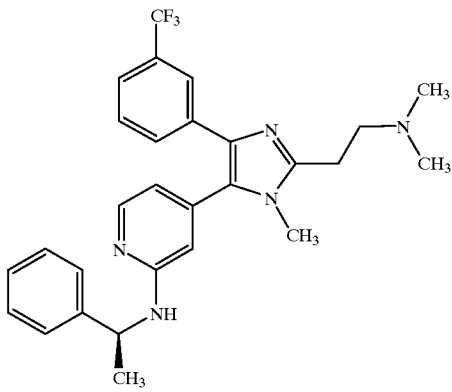

(S)-1-Phenyl-N-{4-[2-(2-dimethylaminoethyl)-3-methyl-5-(3-trifluoromethylphenyl)-3H-imidazol-4yl]-pyridin-2-yl}-ethylamine The compound was prepared as described in example 1 then methylated as described in example 6.

$^1$H NMR (300 MHz, CD$_3$OD) d 8.00 (d, J=5.1 Hz, 1H, Pyr), 7.69 (s, 1H, Ar), 7.50 (d, J=7.6 Hz, 1H, Ar), 7.46 (d, J=7.8 Hz, 1H, Ar), 7.36 (t, J=7.7 Hz, 1H, Ar), 7.31–7.22 (m, 4H, Ar), 7.16 (t, J=6.9 Hz, 1H, Ar), 6.46 (dxd, J=5.1 & 1.5 Hz, 1H, Pyr), 6.34 (s, 1H, Pyr), 4.81 (q, J=6.8 Hz, 1H, PhCHCH$_3$), 3.36 (s, 3H, CH$_3$N), 2.99 (t, J=7.6 Hz, 2H, CH$_2$CH$_2$N), 2.78 (t, J=7.6 Hz, 2H, CCH$_2$CH$_2$), 2.37 (s, 6H, N(CH$_3$)$_2$), 1.48 (d, J=6.8 Hz, 3H, PhCHCH$_3$); MS (FAB) Calcd for C$_{28}$H$_{30}$F$_3$N$_5$ (M+H$^+$) 493.2, found 494.3

The ability of compounds of the present invention to inhibit the synthesis or the activity of cytokines can be demonstrated using the following in vitro assays.

BIOLOGICAL ASSAYS

Lipopolysaccharide Mediated Production of Cytokines

Human peripheral blood mononuclear cells (PBMC) are isolated from fresh human blood according to the procedure of Chin and Kostura, *J. Immunol.* 151, 5574–5585 (1993). Whole blood is collected by sterile venipuncture into 60 mL syringes coated with 1.0 mL of sodium-heparin (Upjohn, 1000 U/mL) and diluted 1:1 in Hanks Balanced Salt Solution (Gibco). The erythrocytes are separated from the PBMC's by centrifugation on a Ficoll-Hypaque lymphocyte separation media. The PBMC's are washed three times in Hanks Balanced Salt Solution and then resuspended to a final concentration of 2×10$^6$ cell/mL in RPMI containing 10% fresh autologous human serum, penicillin streptomycin (10 U/mL) and 0.05% DMSO. Lipopolysaccharide (Salmonella type Re545; Sigma Chemicals) is added to the cells to a final concentration of 100 ng/mL. An aliquot (0.1 mL) of the cells is quickly dispensed into each well of a 96 well plate containing 0.1 mL of the test compound, at the appropriate dilution, and are incubated for 24 hours. at 37° C. in 5% CO2. At the end of the culture period, cell culture supernatants are assayed for IL-1β, TNF-α, IL-6 and PGE2 production using specific ELISA.

IL-1 Mediated Cytokine Production

Human peripheral blood mononuclear cells are isolated from fresh human blood according to the procedure of Chin and Kostura, *J. Immunol.* 151, 5574–5585 (1993). Whole blood is collected by sterile venipuncture into 60 mL syringes coated with 1.0 mL of sodium-heparin (Upjohn, 1000 U/mL) and diluted 1:1 in Hanks Balanced Salt Solution (Gibco). The erythrocytes are separated from the PBMC's by centrifugation on a Ficoll-Hypaque lymphocyte separation media. The PBMC's are washed three times in Hanks Balanced Salt Solution and then resuspended to a final concentration of 2×10$^6$ cell/mL in RPMI containing 10% fresh autologous human serum, penicillin streptomycin (10 U/ml) and 0.05% DMSO. Endotoxin free recombinant human IL-1b is then added to a final concentration of 50 pMolar. An aliquot (0.1 mL) of the cells is quickly dispensed into each well of a 96 well plate containing 0.1 mL of the compound at the appropriate dilution. and are incubated for 24 hours. at 37° C. in 5% CO2. At the end of the culture period, cell culture supernatants are assayed for TNF-a, IL-6 and PGE2 synthesis using specific ELISA.

Determination of IL-1β, TNF-α, IL-6 and Prostanoid Production From LPS or IL-1 Stimulated PBMC's

IL-1β ELISA

Human IL-1β can be detected in cell-culture supernatants or whole blood with the following specific trapping ELISA. Ninety-six well plastic plates (Immulon 4; Dynatech) are coated for 12 hours at 4° C. with 1 mg/mL protein-A affinity chromatography purified mouse anti-human IL-1β monoclonal antibody (purchased as an ascites preparation from LAO Enterprise, Gaithersburg Md.) diluted in Dulbecco's phosphate-buffered saline (—MgCl$_2$, —CaCl$_2$). The plates are washed with PBS-Tween (Kirkegaard and Perry) then blocked with 1% BSA diluent and blocking solution (Kirkegaard and Perry) for 60 minutes at room temperature followed by washing with PBS Tween. IL-1β standards are prepared from purified recombinant IL-1β produced from *E. coli*. The highest concentration begins at 10 ng/mL followed by 11 two-fold serial dilutions. For detection of IL-1β from cell culture supernatants or blood plasma, 10–25 mL of supernatant is added to each test well with 75–90 mL of PBS Tween. Samples are incubated at room temperature for 2 hours then washed 6 times with PBS Tween on an automated plate washer (Dennly). Rabbit anti-human IL-1β polyclonal antisera diluted 1:500 in PBS-Tween is added to the plate and incubated for 1 hour at room temperature followed by six washes with PBS-Tween. Detection of bound rabbit anti-IL-1β IgG is accomplished with Fab' fragments of Goat anti-rabbit IgG-horseradish peroxidase conjugate (Accurate Scientific) diluted 1:10,000 in PBS-Tween. Peroxidase activity was determined using TMB peroxidase substrate kit (Kirkegaard and Perry) with quantitation of color intensity on a 96-well plate Molecular Devices spectrophotometer set to determine absorbance at 450 nM. Samples are evaluated using a standard curve of absorbance versus concentration. Four-parameter logistics analysis generally is used to fit data and obtain concentrations of unknown compounds.

TNF-α ELISA

Immulon 4 (Dynatech) 96-well plastic plates are coated with a 0.5 mg/mL solution of mouse anti-human TNF-a monoclonal antibody. The secondary antibody is a 1:2500 dilution of a rabbit anti-human TNF-α polyclonal serum purchased from Genzyme. All other operations are identical to those described above for IL-1β. The standards are prepared in PBS-Tween+10% FBS or HS. Eleven 2 fold dilutions are made beginning at 20 ng/mL TNF-α.

IL-6 ELISA

Levels of secreted human IL-6 are also determined by specific trapping ELISA as described previously in Chin and Kostura, *J. Immunol.* 151, 5574–5585 (1993). (Dynatech)

ELISA plates are coated with mouse anti-human IL-6 monoclonal antibody diluted to 0.5 mg/mL in PBS. The secondary antibody, a rabbit anti-human IL-6 polyclonal antiserum, is diluted 1:5000 with PBS-Tween. All other operations are identical to those described above for IL-1b. The standards are prepared in PBS-Tween+10% FBS or HS. Eleven 2 fold dilutions are made beginning at 50 ng/mL IL-6.

PGE$_2$ Production

Prostaglandin E2 is detected in cell culture supernatants from LPS or IL-1 stimulated PBMC's using a commercially available enzyme immunoassay. The assay purchased from the Cayman Chemical (Catalogue number 514010) and is run exactly according to the manufacturers instructions.

Interleukin8 (IL-8)

The present compounds can also be assayed for IL-8 inhibitory activity as discussed below. Primary human umbilical cord endothelial cells (HUVEC) (Cell Systems, Kirland, Wash.) are maintained in culture medium supplemented with 15% fetal bovine serum and 1% CS-HBGF consisting of aFGF and heparin. The cells are then diluted 20-fold before being plated (250 µl) into gelatin coated 96-well plates. Prior to use, culture medium is replaced with fresh medium (200 µl). Buffer or test compound (25 µl, at appropriate concentrations) is then added to each well in quadruplicate wells and the plates incubated for 6 h in a humidified incubator at 37° C. in an atmosphere of 5% CO$_2$. At the end of the incubation period, supernatant is removed and assayed for IL-8 concentration using an IL-8 ELISA kit obtained from R&D Systems (Minneapolis, Minn.). All data is presented as mean value (ng/mL) of multiple samples based on the standard curve. IC50 values where appropriate are generated by non-linear regression analysis.

What is claimed is:

1. A compound of the formula

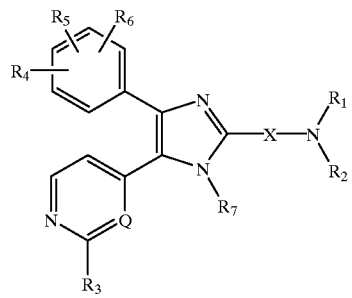

(I)

wherein

X is $C_1$–$C_6$ alkyl, said alkyl group optionally substituted by 1–3 groups selected from halogen, hydroxy, $CF_3$, $NH_2$ and $NO_2$; or a heterocyclic group connected to the imidazole ring by a direct bond or by $C_1$–$C_6$ alkyl;

$R_1$ and $R_2$ are independently hydrogen or $C_1$–$C_6$ alkyl, said alkyl group optionally substituted by 1–3 groups selected from halogen, hydroxy, $CF_3$, $NH_2$ and $NO_2$; or $R_1$ and $R_2$ taken together with the nitrogen atom represent an optionally substituted 4 to 10 membered non-aromatic heterocyclic ring containing at least one N atom, and optionally containing 1–2 additional N atoms and 0–1 O or S atom; or $R_2$ and X taken together represent an optionally substituted 4 to 10 membered non-aromatic heterocyclic ring containing at least one N atom, and optionally containing 1–2 additional N atoms and 0–1 O or S atoms;

Q is CH or N;

$R_3$ is hydrogen or NH($C_1$–$C_6$ alkyl)aryl;

$R_4$, $R_5$ and $R_6$ independently represent a member selected from the group consisting of hydrogen, halo, hydroxy, $CF_3$, $NH_2$, $NO_2$, $C_1$–$C_6$ alkyl, said alkyl group optionally substituted by 1–3 groups selected from halogen, hydroxy, $CF_3$, $NH_2$ and $NO_2$, $C_1$–$C_6$ alkoxy, said alkoxy group optionally substituted by 1–3 groups selected from halogen, hydroxy, $CF_3$, $NH_2$ and $NO_2$; $C_3$–$C_8$ cycloalkyl, said cycloalkyl group optionally substituted by 1–3 groups selected from halogen, hydroxy, $CF_3$, $NH_2$ and $NO_2$ or aryl, said aryl group optionally substituted by 1–3 groups selected from halogen, hydroxy, $CF_3$, $NH_2$ and $NO_2$;

$R_7$ is hydrogen or $C_1$–$C_6$ alkyl, said alkyl group optionally substituted by 1–3 groups selected from halogen, hydroxy, $CF_3$, $NH_2$ and $NO_2$;

or a pharmaceutically acceptable addition salt and/or hydrate thereof, or where applicable, a geometric or optical isomer or racemic mixture thereof.

2. The compound in accordance with claim 1 of the formula

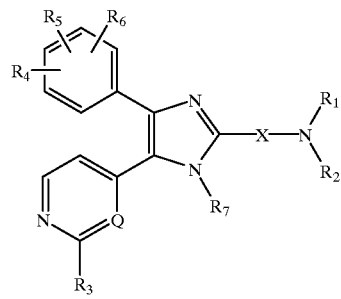

or a pharmaceutically acceptable salt thereof, wherein:

Q is CH;

X is $C_1$–$C_6$ alkyl; or $R_2$ and X taken together represent an azetidine group;

$R_4$, $R_5$ and $R_6$ are independently hydrogen or $CF_3$;

$R_7$ is $CH_3$;

$R_1$ and $R_2$ are independently hydrogen or $C_1$–$C_6$ alkyl; or $R_1$ and $R_2$ taken together with the nitrogen atom form a morpholine group.

3. A compound of the formula:

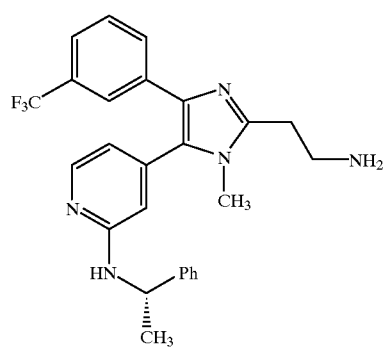

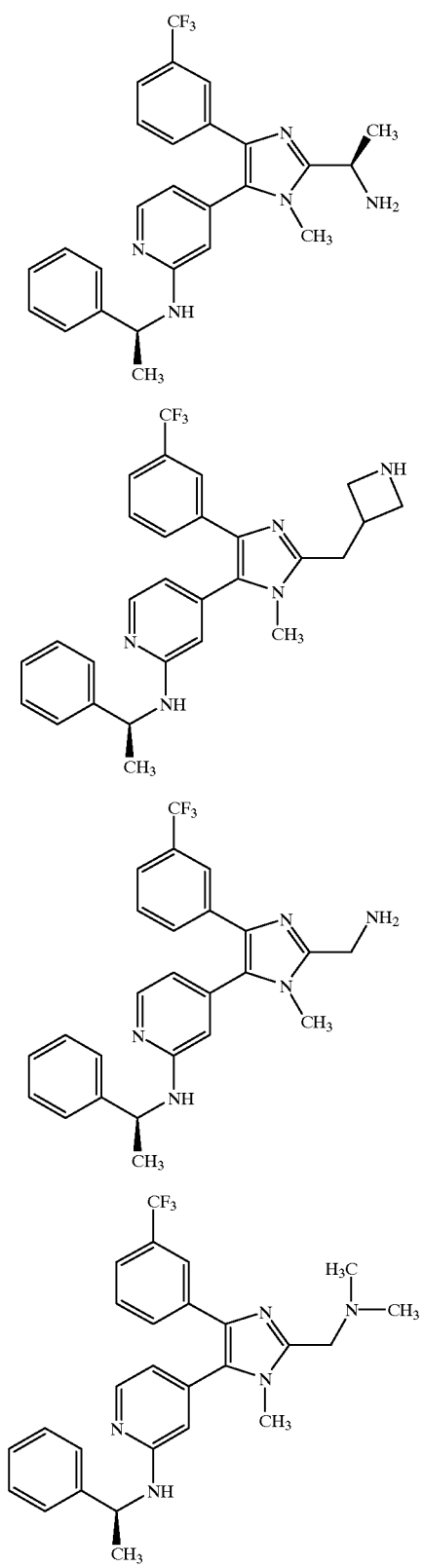
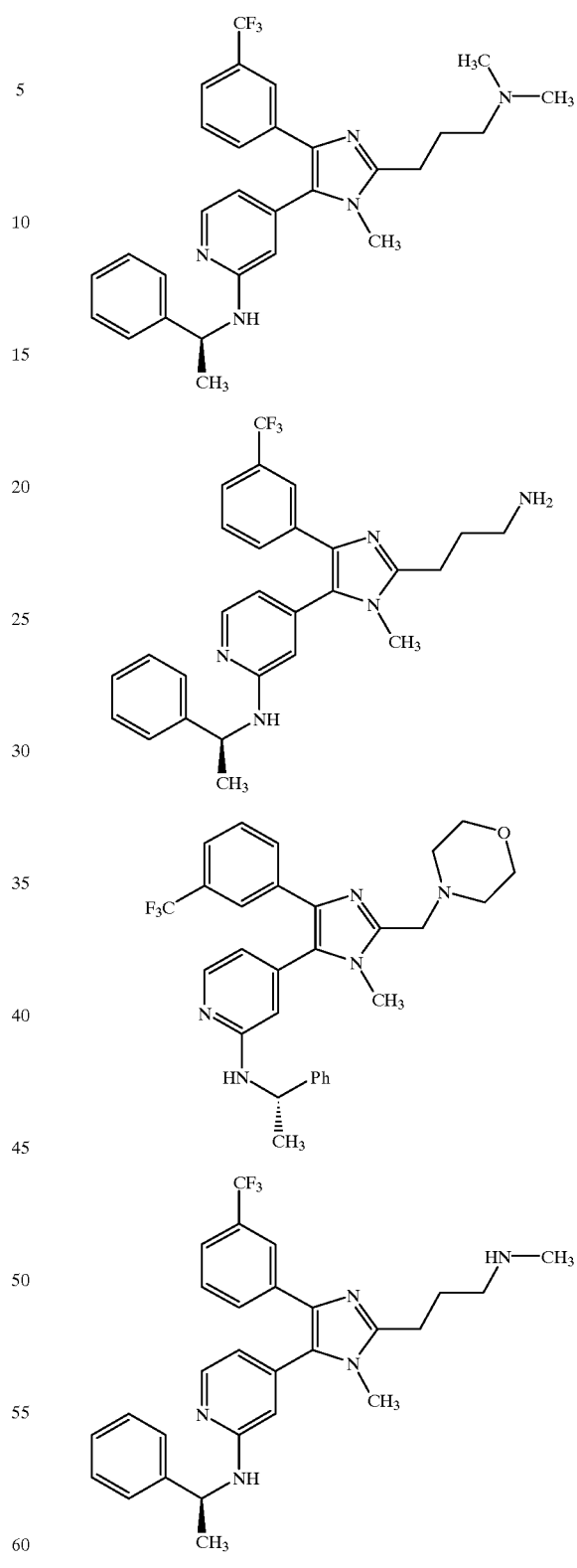

-continued

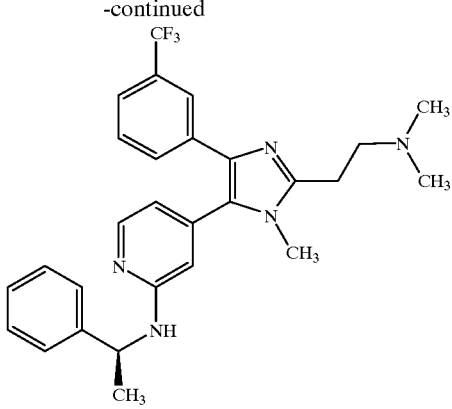

or a pharmaceutically acceptable addition salt and/or hydrate thereof, or where applicable, a geometric or optical isomer or racemic mixture thereof.

4. A pharmaceutical composition which is comprised of a compound in accordance with claim 1 in combination with a pharmaceutically acceptable carrier.

5. A pharmaceutical composition which is produced by combining a compound in accordance with claim 1 and a pharmaceutically acceptable carrier.

6. A method of treating a cytokine mediated disease in a mammal, comprising administering to a mammalian patient in need of such treatment an amount of a compound as described in claim 1 in an amount which is effective to treat said cytokine mediated disease.

7. A method of treating inflammation in a mammalian patient in need of such treatment, which is comprised of administering to said patient an anti-inflammatory effective amount of a compound as described in claim 1.

8. A method in accordance with claim 6 wherein the cytokine mediated disease is rheumatoid arthritis, osteoarthritis, endotoxemia, toxic shock syndrome, inflammatory bowel disease, tuberculosis, atherosclerosis, muscle degeneration, cachexia, psoriatic arthritis, Reiter's syndrome, rheumatoid arthritis, gout, traumatic arthritis, rubella arthritis or acute synovitis.

9. A method in accordance with claim 6 wherein the cytokine mediated disease is rheumatoid arthritis, rheumatoid spondylitis, osteoarthritis, gouty arthritis, sepsis, septic shock, endotoxic shock, gram negative sepsis, toxic shock syndrome, adult respiratory distress syndrome, cerebral malaria, chronic pulmonary inflammatory disease, silicosis, pulmonary sarcosis, bone resorption diseases, reperfusion injury, graft v. host rejection, allograft rejection, fever, myalgia due to infection, cachexia secondary to infection or malignancy, cachexia secondary to acquired immune deficiency syndrome (AIDS), AIDS related complex (ARC), keloid formation, scar tissue formation, Crohn's disease, ulcerative colitis or pyresis.

10. A method of treating osteoporosis in a mammalian patient in need of such treatment, which is comprised of administering to said patient an amount of a compound as described in claim 1 which is effective to treat osteoporosis.

11. A method of treating bone resorption in a mammalian patient in need of such treatment, which is comprised of administering to said patient an amount of a compound as described in claim 1 which is effective to treat bone resorption.

12. A method of treating Crohn's disease in a mammalian patient in need of such treatment which is comprised of administering to said patient an amount of a compound as described in claim 1 which is effective to treat Crohn's disease.

13. A process for making a pharmaceutical composition comprising combining a compound of claim 1 and a pharmaceutically acceptable carrier.

* * * * *